(12) United States Patent
Weinfield (10) Patent No.: US 7,793,666 B2
(45) Date of Patent: Sep. 14, 2010

(54) APPARATUS AND METHOD FOR TREATMENT OF INFECTED NAIL

(75) Inventor: Todd A. Weinfield, Redwood City, CA (US)

(73) Assignee: Innovation Biomedical Devices, Inc., Redwood City, CA (US)

( * ) Notice: Subject to any disclaimer, the term of this patent is extended or adjusted under 35 U.S.C. 154(b) by 283 days.

(21) Appl. No.: 11/423,874

(22) Filed: Jun. 13, 2006

(65) Prior Publication Data

US 2007/0027481 A1    Feb. 1, 2007

Related U.S. Application Data

(60) Provisional application No. 60/704,230, filed on Jul. 28, 2005, provisional application No. 60/709,602, filed on Aug. 8, 2005, provisional application No. 60/731,754, filed on Oct. 30, 2005.

(51) Int. Cl.
```
A45D 29/20    (2006.01)
A45D 29/00    (2006.01)
A45D 29/18    (2006.01)
A61F 7/00     (2006.01)
A61F 7/12     (2006.01)
A61M 35/00    (2006.01)
A61N 1/39     (2006.01)
```

(52) U.S. Cl. ............... 132/74.5; 132/73; 132/73.5; 604/291; 604/292; 604/289; 607/96; 607/1

(58) Field of Classification Search ............ 607/1; 604/292, 291, 289; 132/74.5
See application file for complete search history.

(56) References Cited

U.S. PATENT DOCUMENTS

| 3,298,368 A | 1/1967 | Charos |
| 3,864,847 A | 2/1975 | Friedman et al. |
| 3,930,320 A | 1/1976 | Henderson |
| 4,087,675 A * | 5/1978 | Sansonetti ............... 604/292 |
| 4,230,105 A | 10/1980 | Harwood |
| 4,267,852 A * | 5/1981 | Hullinger .................. 132/73 |

(Continued)

FOREIGN PATENT DOCUMENTS

JP    06-057323    8/1994

(Continued)

OTHER PUBLICATIONS

Thomas, M.D., Dwight, "How I Won the War on Toenail Fungus," www.BottomLineSecrets.com, Feb. 15, 2006. 1 p.

(Continued)

*Primary Examiner*—Tatyana Zalukaeva
*Assistant Examiner*—Susan Su
(74) *Attorney, Agent, or Firm*—Syndicated Law PC; Brian S. Boyer (57) ABSTRACT

An infected nail of a digit of a patient is treated using apparatus including an enclosure capable of housing at least a distal end of at least one digit of a patient having an infected nail. The apparatus also includes a heater and a nail infection agent-containing member housed within the enclosure and positionable against an infected nail at the distal end of a digit housed within the enclosure. The heater is in heat-transfer relationship with the nail infection agent. In this way heated nail infection agent can be maintained against an infected nail by the nail infection agent-containing member.

19 Claims, 7 Drawing Sheets

U.S. PATENT DOCUMENTS

| | | | |
|---|---|---|---|
| 4,331,137 A | 5/1982 | Sarui | |
| 4,556,055 A | 12/1985 | Bonner, Jr. | |
| 4,702,246 A | 10/1987 | Ellis et al. | |
| 4,754,769 A | 7/1988 | Flynn | |
| 4,846,176 A | 7/1989 | Golden | |
| 4,962,761 A | 10/1990 | Golden | |
| 5,098,415 A | 3/1992 | Levin | |
| 5,156,591 A * | 10/1992 | Gross et al. | 604/20 |
| 5,181,914 A * | 1/1993 | Zook | 604/307 |
| 5,431,622 A | 7/1995 | Pyrozyk et al. | |
| 5,449,658 A | 9/1995 | Unhoch et al. | |
| 5,668,084 A | 9/1997 | Unhoch et al. | |
| 5,696,164 A | 12/1997 | Sun et al. | |
| 5,795,314 A | 8/1998 | Berenstein | |
| 6,042,845 A | 3/2000 | Sun et al. | |
| 6,095,992 A | 8/2000 | Augustine | |
| 6,231,875 B1 | 5/2001 | Sun et al. | |
| 6,235,047 B1 | 5/2001 | Augustine et al. | |
| 6,245,347 B1 | 6/2001 | Zhang et al. | |
| 6,261,595 B1 | 7/2001 | Stanley et al. | |
| 6,281,239 B1 | 8/2001 | Glassman | |
| 6,436,063 B1 | 8/2002 | Augustine et al. | |
| 6,453,648 B1 | 9/2002 | Zhang et al. | |
| 6,465,709 B1 | 10/2002 | Sun et al. | |
| 6,477,410 B1 * | 11/2002 | Henley et al. | 604/20 |
| 6,485,506 B2 | 11/2002 | Augustine | |
| 6,528,697 B1 | 3/2003 | Knutson et al. | |
| 6,585,670 B2 | 7/2003 | Augustine et al. | |
| 6,585,963 B1 | 7/2003 | Quan et al. | |
| 6,589,270 B2 | 7/2003 | Augustine | |
| 6,634,367 B2 * | 10/2003 | Abraham et al. | 132/74.5 |
| 6,641,601 B1 | 11/2003 | Augustine et al. | |
| 6,727,401 B1 | 4/2004 | Venkateshwaran et al. | |
| 6,735,470 B2 | 5/2004 | Henley et al. | |
| 6,756,053 B2 | 6/2004 | Zhang et al. | |
| 6,780,426 B2 | 8/2004 | Zhang et al. | |
| 6,821,508 B2 | 11/2004 | Zatz et al. | |
| 6,846,837 B2 | 1/2005 | Maibach et al. | |
| 6,881,418 B2 | 4/2005 | Morita et al. | |
| 6,921,529 B2 | 7/2005 | Maley | |
| 6,955,819 B2 | 10/2005 | Zhang et al. | |
| 7,052,167 B2 | 5/2006 | Vanderschuit | |
| 2002/0007191 A1 | 1/2002 | Feldman | |
| 2003/0144625 A1* | 7/2003 | Sherman et al. | 604/20 |
| 2003/0225441 A1 | 12/2003 | Boynton et al. | |
| 2004/0096410 A1 | 5/2004 | Maley et al. | |
| 2004/0161452 A1 | 8/2004 | Petit | |
| 2006/0013862 A1 | 1/2006 | Held | |
| 2006/0052739 A1 | 3/2006 | Henley et al. | |
| 2006/0234981 A1 | 10/2006 | Baker et al. | |
| 2007/0027481 A1 | 2/2007 | Weinfield | |
| 2007/0049998 A1 | 3/2007 | Conrad et al. | |
| 2007/0104664 A1* | 5/2007 | Maltezos et al. | 424/61 |
| 2007/0155699 A1 | 7/2007 | Baker et al. | |
| 2007/0265226 A1 | 11/2007 | Lee et al. | |
| 2008/0312579 A1* | 12/2008 | Chang et al. | 604/20 |
| 2009/0048590 A1 | 2/2009 | Conrad et al. | |

FOREIGN PATENT DOCUMENTS

| | | |
|---|---|---|
| JP | 07-028521 | 5/1995 |
| JP | 2003-123136 | 5/2003 |
| JP | 2006-075357 | 3/2006 |

OTHER PUBLICATIONS

U.S. Appl. No. 60/730,545 entitled Treatment of Toenail Fungus, filed Oct. 26, 2005, 1 pp.

U.S. Appl. No. 60/730,545, filed Oct. 26, 2005, Maltezos, et al.

Ashburn, M. A., et al., The Pharmacokinetics of Transdermal Fentanyl Delivered With and Without Controlled Heat, *The Journal of Pain*, vol. 4, Issue 6, Aug. 2003, 291-297.

Baran, R., et al., *Textbook of Cosmetic Dermatology*, 2004, p. 58.

Botek, G., Fungal Nail Infection: Assessing the New Treatment Options, *Cleveland Clinic Journal of Medicine*, 2003, 70(2), 110-114.

Burge, H., How Does Heat Affect Fungi? *The Environmental Reporter*, Mar. 2006, vol. 4, Issue 3.

Chato, J., Electrical Engineer, An Oral History Conducted in 2000 by Frederik Nebeker, IEEE History Center, Rutgers University, New Brunswick, NJ.

Chato, J.C., Thermal Therapy of Toe Nail Fungus, Advances in Heat and Mass Transfer in Biotechnology 2000, *Advances in Heat and Mass Transfer in Biotechnology 2000*, Nov. 5-10, 2000, 139-140.

Gupchup-Malhotra, G., et al., Characterization of the Physical Factors Affecting Nail Permeation Using Water as a Probe, Journal of Cosmetic Science, 51:6, 367-377 (2000).

Hull, W., Heat-Enhanced Transdermal Drug Delivery: A Survey Paper*, *The Journal of Applied Research*, vol. 2, No. 1, Winter 2002.

Jaffre., R. Onychomycosis. Arch Fam Med., 7, 1988, 587-592.

Kobayashi, Y., et al., Drug Permeation Through the Three Layers of the Human Nail Plate, Journal of Pharmacy and Pharmacology, Mar. 1, 1999, 51:3, 271-278.

Kobayashi, Y., et al., In vitro Permeation of Several drugs Through the Human Nail Plate: Relationship Between Physiochemical Properties and Nail Permeability of Drugs, European Journal of Pharmaceutical Sciences, 21:4, 471-47, Mar. 2004.

Lamberg, S.I., Blackwell's Primary Care Essentials: Dermatology, Second Edition, 2002.

Leeming, M.N. et al., Low-Voltage, Direct-Current Burns, *JAMA*, Nov. 30, 1970, vol. 214, No. 9, 1681-1684.

Mertin, D., et al., In Vitro Permeability of the Human Nail and a Keratin Membrane from Bovine Hooves: Prediction of the Penetration Rate of Antimycotics Through the Nail Plate and their Efficacy, Journal of Pharmaceutics and Pharmacology. 49:866-872 (1997).

Moritz A.R. et al., Studies of Thermal Injury II: The Relative Importance of Time and Surface Temperature in the Causation of Cutaneous Burn, *AM J Pathol*, 1947, 23, 695-720.

Murdan, S., Drug Delivery to the Nail Following Topical Application, International Journal of Pharmaceutics, 236:1-2, Apr. 2002, 1-26.

Quintanar-Guerrero, D., et al., The Effect of Keratolytic Agents on the Permeability of Three Imidazole Antimycotic Drugs Through the Human Nail, *Drug Dev Ind Pharm*, vol. 24, Issue 7, Jul. 1998, 685-690.

Reinauer, S. et al., Iontophoresis With Alternating Current and Direct Current Offset (AC/DC Iontophoresis): A New Approach for the Treatment of Hyperhidrosis, *British Journal of Dermatology*, vol. 129, Issue 2, Aug. 1993, 166-169.

Roberts, D.F., et al., A Possible Climatic Effect on Nail Growth, Journal of Applied Physiology, 13: 135-138 (1958).

Robbins, C.R., *Chemical and Physical Behavior of Human Hair*, 4th Ed. 2004 pp. 238.

Scifers, J.R., Iontophoresis: Maximizing Treatment Effectivenes,[online] [retrieved Aug. 11, 2009] URL: http://www.hnppharmaceuticals.com/pub_dwnlds/pdf/therapists/Ionto/Ionto_Max_effectivness.pdf.

Shoemaker, T.S., et al., A Pilot Study Assessing the Impact of Heat on the Transdermal Delivery of Testosterone, *J Clin Pharmacol*, 2001; 41: 677-682.

Speakman, J., The Micelle Structure of the Wool Fibre, J. Proc. R. Soc Lond. A 1931 132, 167-191.

Speakman, J., Elliot, G. Symposium on Fibrous Proteins, Soc. Dyers Col., Leeds, UK vol. 116 (1946).

Swarbrick J., *Encyclopedia of Pharmaceutical Technology*, Oct. 2006 p. 3848.

Timby, B.K. et al., *The Essentials of Nursing: Care of Adults and Children*, 2005, 928.

Turley, S. M., Second-Degree Burn From Iontophoresis, [online] Apr. 15, 2008 [retrived Aug. 11, 2009] Consultant, vol. 48 No. 5. URL: http://www.consultantlive.com/photoclinic/article/10162/1156010.

Walters, K. A., et al., Physiochemical Characterization of the Human Nail: I. Pressure Sealed Apparatus for Measuring Nail Plate Permeabilities, Journal of Investigative Dermatology, 76:2, Feb. 1981,76-79.

A Trans-Keratin Drug Delivery System for Onychomycosis, Annual Meeting, Council for Nail Disorders, Feb. 1, 2007. URL: http://www.aad.org/meetings/previous/_doc/Posters_2007%20Annual%20Meeting.pdf.

Lesions and Shocks During Iontophoresis [online] [retrived on Aug. 11, 2009] URL: http://mdsr.ecri.org/summary/detail.aspx?doc_id=8170.

International Search Report, Jan. 27, 2010, Innovation Biomedical Devices, Inc.

* cited by examiner

APPARATUS AND METHOD FOR TREATMENT OF INFECTED NAIL

CROSS-REFERENCE TO OTHER APPLICATIONS

This application claims the benefit of the following provisional patent applications: 60/704,230 filed on 28 Jul. 2005 and entitled Liquid Heater Capsule for Treatment of Onychomycosis and Other Nail Infections; 60/709,602 filed on 8 Aug. 2005 and entitled Protective Glove for Hand or Foot during Submersion Nail Treatment; and 60/731,754 filed on 30 Oct. 2005 and entitled Liquid Heater Compress for Treatment of Onychomycosis and Other Nail Infections.

FEDERALLY SPONSORED RESEARCH OR DEVELOPMENT

None.

BACKGROUND OF THE INVENTION

Tinea unguium or onychomycosis (nail fungus) has long been a medical challenge to cure. While there are topically applied reagents which effectively control fungal growth (e.g., cyclopirox) getting the reagent to thoroughly contact the fungus has long been the challenge. The nail provides a seemingly impenetrable membrane protecting the fungus from outside elements as Quintanar-Guerrero et al from Universidad Nacional Autónoma de México have shown in their paper, The effect of keratolytic agents on the permeability of three imidazole antimycotic drugs through the human nail (Drug Dev Ind Pharm, Jul. 1, 1998; 24(7): 685-90).

Current topical treatment research has focused on developing a single reagent which both penetrates the nail and destroys the fungus. Unfortunately, to date such research has not produced this cure. Ciclopirox (Penlac, Loprox) alone has a cure rate of just 20% after one year, however, this rate may include data for Ciclopirox' primary purpose, that is, tinea corporis. Part of the challenge is developing a single treatment for the 119 known strands of tinea.

Quintanar-Guerrero et al also found that keratolytic substances such as papain, and salicylic acid used in combination did enhance the permeability of the antimycotic.

Patents with methods, formulae, and apparatus to increase the permeability of the antimycotic through the nail into the nail bed dominate this art See, for example, the following U.S. patents and patent application publications: U.S. Pat. Nos. 6,821,508; 6,921,529; 5,795,314; 5,098; 4,331,137; 2004/0161452 A1; 2006/0013862; 6,727,401; 6,465,709.

BRIEF SUMMARY OF THE INVENTION

A first aspect of the invention is directed to apparatus for treating an infected nail of a digit of a patient. The apparatus includes an enclosure capable of housing at least a distal end of at least one digit of a patient having an infected nail. The apparatus also includes a heater and a nail infection agent-containing member housed within the enclosure and positionable against an infected nail at the distal end of a digit housed within the enclosure. The heater is in heat-transfer relationship with the nail infection agent. In this way heated nail infection agent can be maintained against an infected nail by the nail infection agent-containing member.

A second aspect of the invention is also directed to apparatus for treating an infected nail of a digit of a patient. The apparatus includes means for housing at least a distal end of at least one digit of a patient having an infected nail. The apparatus also includes means, within the housing means, for positioning a nail infection agent-containing member against an infected nail at the distal end of a digit housed within the enclosure. In addition, the apparatus includes means for heating the nail infection agent. The nail infection agent can thereby be maintained against an infected nail by the agent-containing member.

A third aspect of the invention is directed to a method for treating an infected nail of a digit of a patient. At least a distal end of at least one digit of a patient, having an infected nail, is housed within an enclosure. A nail infection agent-containing member is positioned against an infected nail at the distal end of a digit housed within the enclosure. The nail infection agent is heated to enhance the effectiveness of the nail infection agent. The heated nail infection agent is maintained against the infected nail for a therapeutically effective time period. In some embodiments the nail infection agent is restrained or prevented from coming into contact with a patient's skin. The nail infection agent may also be restrained or prevented from escaping from the enclosure.

Various features and advantages of the invention will appear from the following description in which the preferred embodiments have been set forth in detail in conjunction with the accompanying drawings.

DETAILED DESCRIPTION OF THE INVENTION

The following description of the invention will typically be with reference to specific structural embodiments and methods. It is to be understood that there is no intention to limit the invention to the specifically disclosed embodiments and methods but that the invention may be practiced using other features, elements, methods and embodiments. Preferred embodiments are described to illustrate the present invention, not to limit its scope, which is defined by the claims. Those of ordinary skill in the art will recognize a variety of equivalent variations on the description that follows. Like elements in various embodiments are commonly referred to with like reference numerals.

The Treatment Apparatus of Preferred Embodiment

The design intent for the embodiment of FIGS. 1-4 is to facilitate the contact between the solution, that is the nail infection agent, and the infected nail(s) N while minimizing the contact between skin S and the solution; and to provide a convenient, portable, and disposable, and/or reusable means to apply solution to the infected nails.

Figure 1:
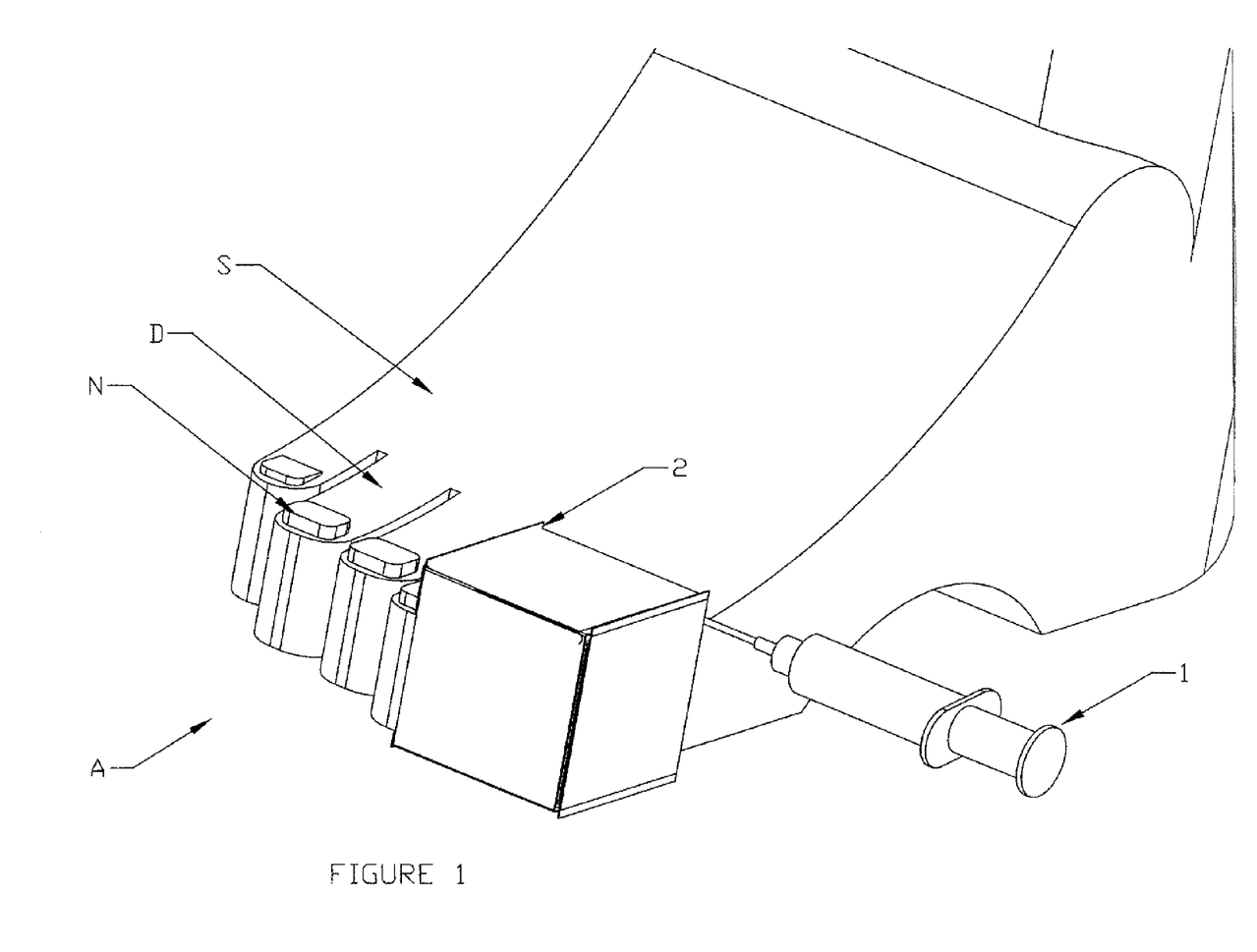
FIG. 1 is a first simplified isometric view of a first preferred embodiment of an infected nail treatment apparatus mounted to a digit of a user.
Figure 2:
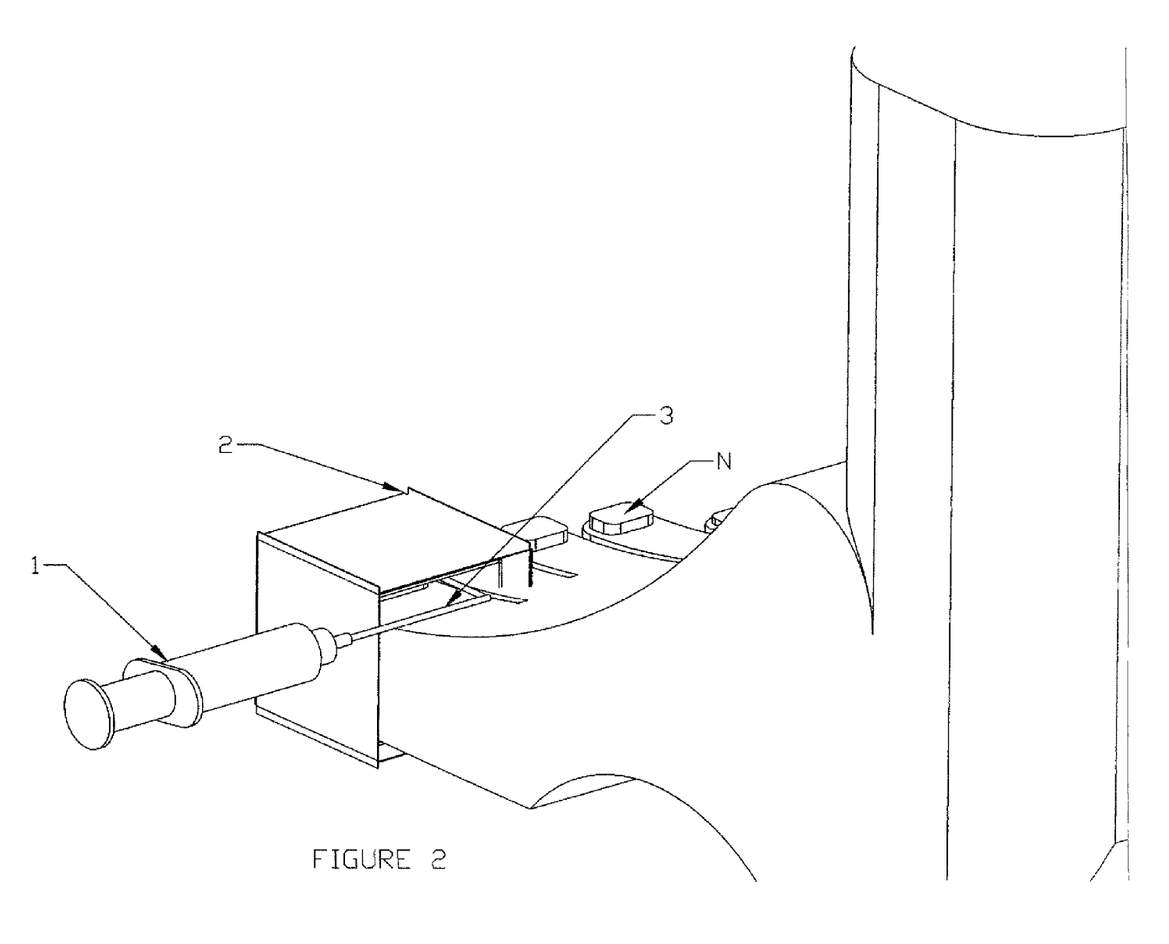
FIG. 2 is a second simplified isometric view of the apparatus of FIG. 1.

Treatment apparatus A includes a reservoir 1 which supplies sponge 5 with solution. Reservoir 1 may be designed as a container which supplies sponge 5 with solution via gravity feed through fluid tubing 3, or (as illustrated in FIGS. 1 and 2) as an electronically controlled pump feed system through fluid tubing 3, or as syringe feed through fluid tubing 3. See Table A for an example of syringe feed which may be purchased as a commercial part. Although sponge 5 may be provided filled with solution, the use of some sort of solution reservoir permits sponge 5 to be supplied and re-supplied with solution as needed during a procedure.

Treatment apparatus A also includes an enclosure 21 which acts as the compress which holds all of the components together including pressing and keeping sponge 5 on top of the infected nail. Enclosure 21 is made of flexible, stretchy hook and loop type of material which adheres to itself similar to a diaper to fasten the invention around the toe(s), and to provide a thermal barrier between sodium acetate heater 4 and the outside. Enclosure 21 also acts to force heater 4 and sponge 5 against infected toe or finger nail(s) to provide an even distribution of both heat and solution and as a liquid barrier between the entire assembly and its surroundings. Enclosure 21 may be designed to accommodate only one nail or as many as ten.

Fluid tubing 3 is the conduit through which reservoir 1 supplies sponge 5 with solution. Corrosion resistant material choices for fluid tubing 3 include ETFE, PTFE, PFA, FEP, and Chemfluor. See Table A for an example of fluid tubing 3 available for purchase in ETFE material.

Sodium acetate heater 4 is a flexible plastic enclosure that contains sodium acetate disk and water. When the sodium acetate disk is clicked (fingernail tap) to mix with the water, the mixture changes to its solid state in an exothermic reaction to freeze at 130 F thereby heating the solution enclosed in sponge 5. The process is reversible by boiling the solid back into the liquid state. Sodium acetate is a food additive and is non-toxic. An example of a sodium acetate heater that may be purchased as a commercial part is included in table A. Other types of heaters may be used and may also be affixed to reservoir 1 or between reservoir 1 and sponge 5 to perform the same function.

The purpose of sponge 5 is to absorb and saturate heated solution onto the infected nail(s), to maintain the solution on the surface of the nail, to isolate the surrounding skin from the solution as much as possible, and to apply heated solution to an irregularly shaped nail (not flat). Sponge 5 receives solution from reservoir 1 through tubing 3. For this reason, sponge 5 may be made from a variety of absorbent sponge/cloth type materials, an example of which is included in Table A. It may be desired to use some type of seals surrounding sponge 5 to help prevent the heated solution from contacting the user's skin.

Sodium polyacrylate liner 21 is the liner between sponge 5 and heater 4 having the same outline as diaper enclosure 2 and may be made from a variety of sponge/cloth type materials (including sodium polyacrylate to absorb excess solution) an example of which is included in Table A. Sodium polyacrylate is the chemical in baby diapers to absorb moisture.

Intended Use of Preferred Embodiment

Treatment apparatus A creates a volume which contains and heats a solution around infected nail(s) to amplify the keratolytic properties of the solution to theoretically imbed the solution within the nail molecular structure, in addition to etching the nail from the top.

Figure 3:
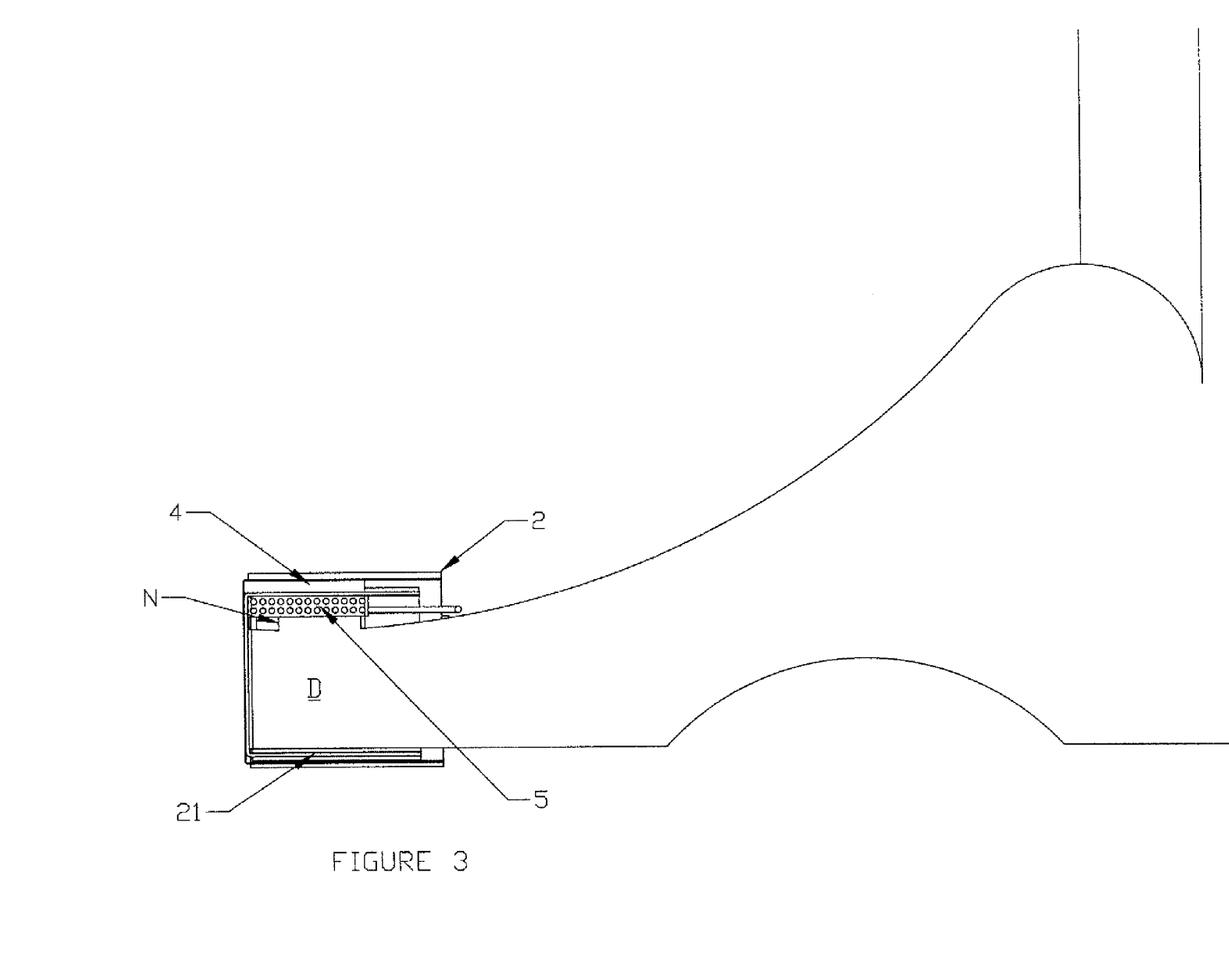
FIG. 3 is a simplified cross-sectional view of the apparatus of FIG. 1.
Figure 4:
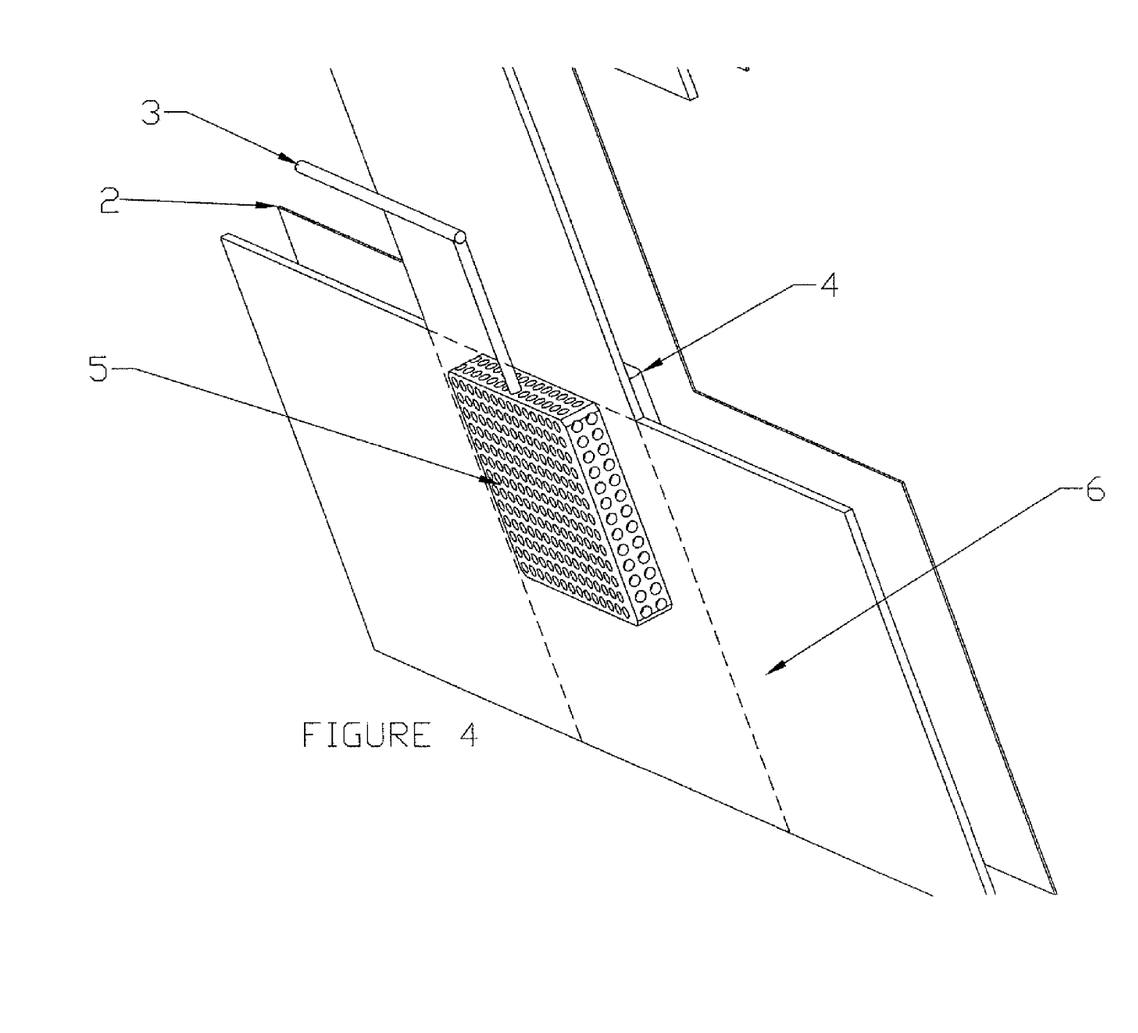
FIG. 4 is a simplified isometric view of the apparatus of FIG. 1 in an unfolded state.

To use treatment apparatus A, infected nail(s) are wrapped into diaper enclosure 2 shown in FIGS. 1-3, preferably creating a liquid tight seal, to force solution-saturated sponge 5 against the infected nail(s). The appropriate chemistry solution (see the discussed below) is added to reservoir 1 which fills sponge 5 with solution. The sodium acetate heater is clicked with a fingernail to heat the solution in sponge 5. Solution is removed from sponge 5 using aspiration of reservoir 1 as necessary.

The Treatment Apparatus of Alternative Embodiment

Figure 5:
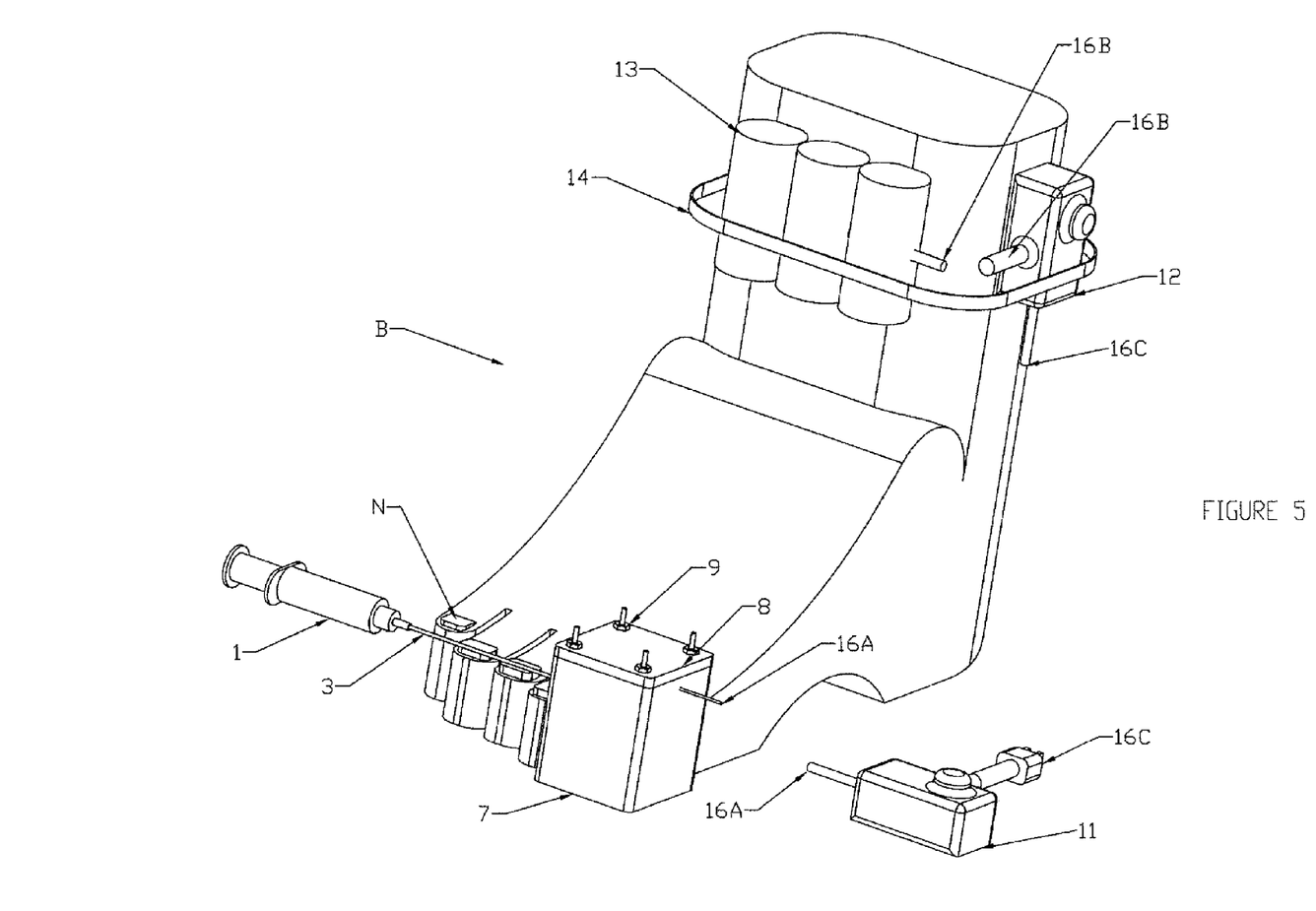
FIG. 5 is a first simplified isometric view of a second, alternative embodiment of an infected nail treatment apparatus mounted to a digit of a user.
Figure 6:
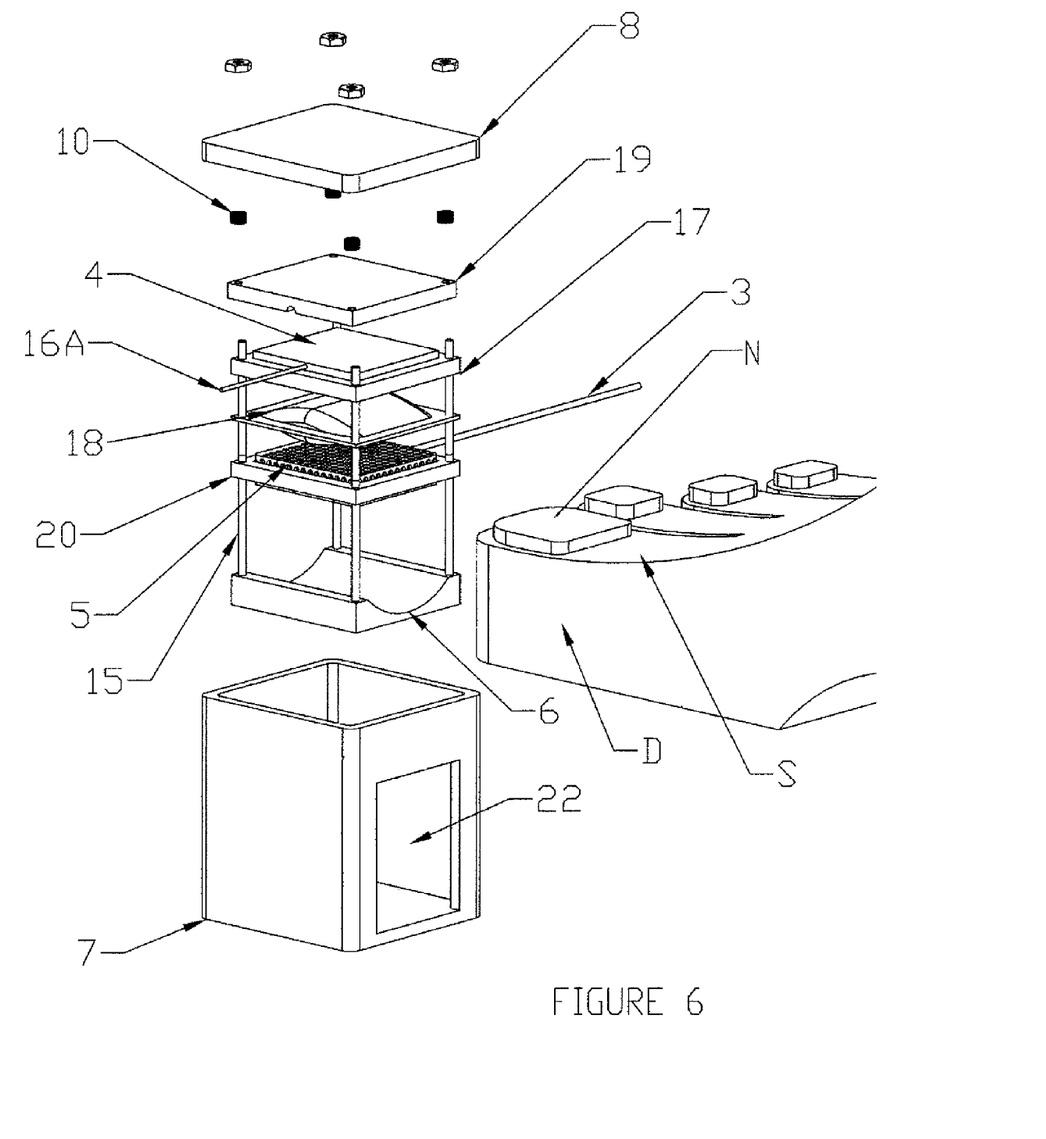
FIG. 6 is an exploded isometric view of the apparatus of FIG. 5.
Figure 7:
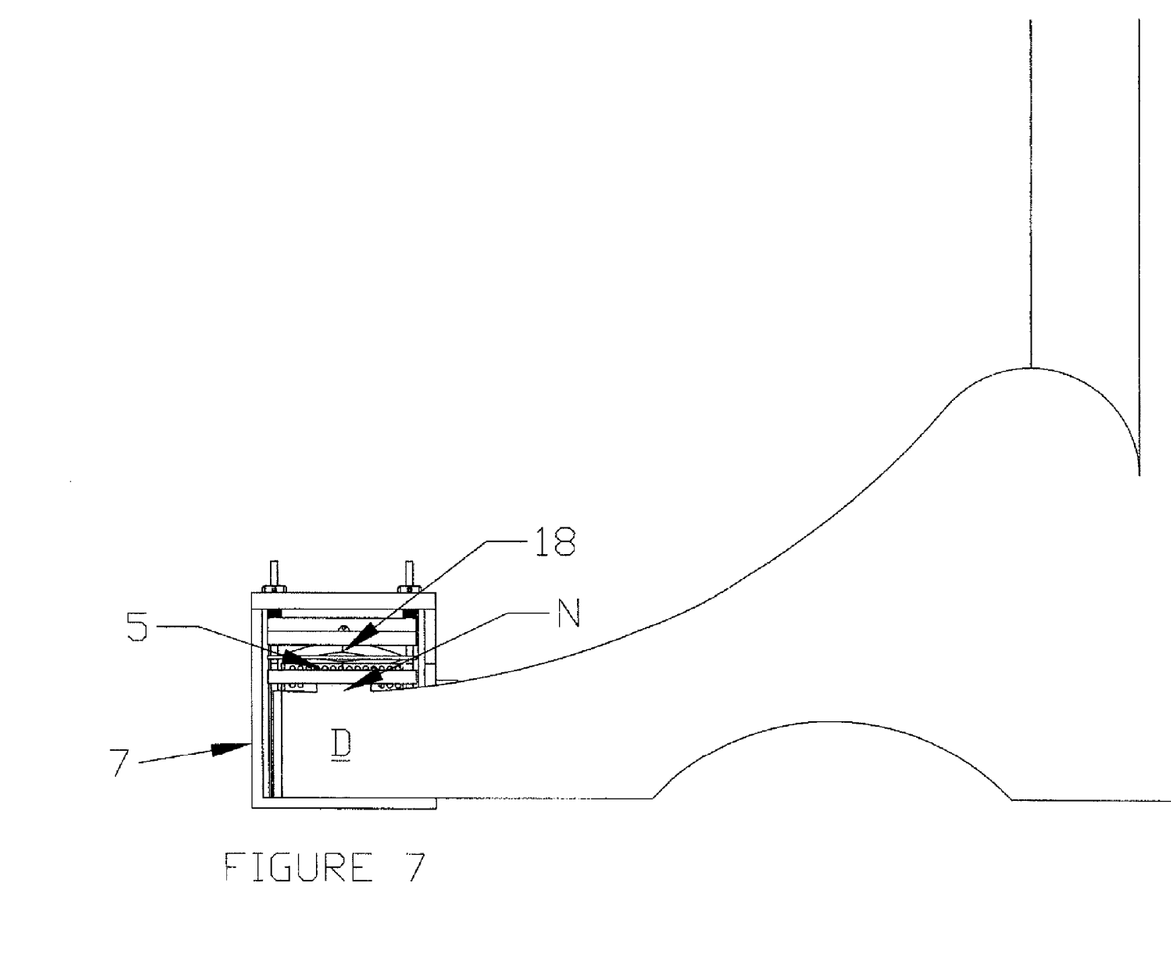
FIG. 7 is a simplified cross-sectional view of the apparatus of FIG. 5.

Treatment apparatus B of FIGS. 5-7 includes a sponge 5 is to absorb and saturate heated solution onto the infected nail(s), to maintain the solution on the surface of the nail, to isolate the surrounding skin from the solution as much as possible, and to apply heated solution to an irregularly shaped nail (not flat). Sponge 5 receives solution from reservoir 1 through tubing 17. For this reason, sponge 5 may be made from a variety of absorbent sponge/cloth type materials, an example of which is included in Table A. Sponge harness 20 is a frame which surrounds and captures sponge 5 for vertical adjustable mounting to threaded rods 15.

The center of sponge harness 20 is open to allow sponge 5 to extend beyond sponge harness 20 to allow sponge 5 to contact the nail with solution. This design allows for vertical adjustment of sponge 5 and sponge harness 20 within enclosure 7 perpendicular to the nail to provide pressure between the nail plate and sponge 5 for thorough distribution of solution onto the nail. Likewise a variety of materials would be appropriate for sponge harness 20, preferably corrosion resistant ones such as 316 L stainless steel or chemically resistant plastics as polycarbonate.

The design intent for fluid-containing, conformable heat transfer device 18 is to evenly distribute heat from the flat regular surface of heater plate 17 to the irregular surface of sponge 5 as it conforms to the irregular nail surface. Device 18 can be made from most flexible water tight plastics (see example in Table A) with a heat transfer fluid such as water trapped inside. The heat transfer fluid inside device 18 contacts the walls of its plastic enclosure and flows inside the plastic evenly distributing the heat from heater 4 and heater plate 17 to sponge 5. The flexible plastic of device 18 is smoothed, hardened and flattened at its edges with holes added for vertical adjustment on threaded rods 15.

Heater 4 is a standard flexible heater available from many suppliers and is usually made by embedding resistance wires inside a thermally flexible rubber material (see Table A) and its temperature is controlled with a heater controller such as item 11 or 12. Heater 4 may be purchased with a pressure sensitive adhesive on one side to secure the heater and for a good thermal connection with heater plate 17. Heater 4 may also be affixed to reservoir 1 to perform the same function.

Heater cover 19 is made from a high temperature thermally isolating material such as polyamide-imide. The center portion of heater cover 19 is scalloped so only the edges contact heater plate 17 to limit heat transfer even further. Heater cover 19 is designed to thermally isolate heater 4 from enclosure cover 8. Heater cover 19 includes holes through which travel threaded rods 15 for vertical adjustment.

Toe harness 6 is designed to comfortably secure toes or fingers within enclosure 7. Materials of choice for toe harness 6 include corrosion resistant metals such as 316 L stainless steel and plastics such as polycarbonate. Threaded rods 15 are permanently and perpendicularly fixed to toe harness 6 using an appropriate adhesive, sonic, solvent bond, or internal or external fastener, and do not move. Toe harness 6 is permanently attached to enclosure 7 using an appropriate fastener means as above and likewise does not move.

Enclosure 7 surrounds, thermally isolates, and preferably creates a liquid barrier between the entire assembly and its surroundings. Enclosure 7 should be made of a corrosion resistant metal such as 316 L stainless steel or plastic such as polycarbonate. Enclosure 7 includes an opening 22 for receipt of digit(s) D, that is the finger(s) or toe(s), with the infected nail(s). Enclosure components may be designed to accommodate only one digit or as many as ten.

Enclosure cover 8 further seals enclosure 7 and the entire assembly from its surroundings and may be made from a semi-high temperature semi-hard rubber material such as EPDM rubber (Shore A 60). Enclosure cover 8 does not move relative to enclosure 7.

Hex nut 9 should be made from a corrosive resistant metal such as 316 L stainless steel to keep threads from galling (see Table A). When hex nut 9 is tightened on threaded rods 15 against enclosure cover 8, it compresses springs 10 forcing heater 4, heater plate 17, fluid 18, sponge 5 and sponge harness 20 against the infected toe nail(s) to provide an even distribution of both heat and solution to the nail(s).

Spring 10 should be made of 316 L stainless steel or other material to withstand both corrosion and repeated tension and compression. The design intent for spring 10 is to provide the spring tension force that compresses the above components into a good thermal and liquid contact with the infected nail(s) against enclosure cover 8.

AC heater controller 11 regulates heater 4 (by modulating power from the wall outlet to heater 4) to selected temperatures. AC heater controller 11 is purchased as a commercial part as shown in Table A. Regulating the temperature in AC heater controller 11 also regulates the temperature of heater plate 17, device 18 and sponge 5. Sponge 5 controls the temperature of the solution on the infected nail which is optimized according to the selected treatment chemistry.

Battery heater controller 12 performs the same function as AC heater controller 11, with the exception that it draws its power from battery pack 13 instead of the wall outlet and is purchased as a commercial component and modified to operate to use battery power instead of AC power. Battery heater controller 12 coupled with battery pack 13 enables the entire assembly to be portable.

Battery pack 13 supplies the power to operate the assembly when in portable mode and may be purchased from a supplier as shown in Table A. Battery pack 13 may be made from a variety of rechargeable battery technologies including NiMH, Lithium Ion, or a hydrogen fuel cell.

Leg harness 14 removeably attaches battery heater controller 12 and battery pack 13 to the limb for portable operation. Leg harness 14 may be made from a variety of materials including nylon fabric, leather, or plastic straps. See Table A for an example of a harness which may be purchased as a commercial part.

Reservoir 1 supplies sponge 5 with solution. Reservoir 1 may be made of a variety of corrosion resistant materials including polycarbonate and 316 L stainless steel. Reservoir 1 may be designed as a container which supplies sponge 5 and the above volumes with solution via gravity feed through fluid tubing 3, or as an electronically controlled pump feed system through fluid tubing 3, or as syringe feed through fluid tubing 3. See Table A for an example of syringe feed which may be purchased as a commercial part.

Threaded rod 15 is the shaft on which the entire assembly travels in a vertical direction perpendicular to the nail. Threaded rod 15 should be made of corrosion resistant material such as 316 L stainless steel. See Table A for an example of a threaded rod which is available for purchase as a commercial component.

Fluid tubing 3 is the conduit through which reservoir 1 supplies sponge 5 and the volumes above with solution. Corrosion resistant material choices for fluid tubing 3 include ETFE, PTFE, PFA, FEP, and Chemfluor. See Table A for an example of fluid tubing 3 available for purchase in ETFE material.

Electrical wire 16 is subdivided into three groups 16A, 16B, and 16C depending on the electrical connection. 16A electrical wire designates the connection between heater 4 and AC heater controller 11. 16B designates the connection between battery pack 13 and battery heater controller 12. 16C designates the connection between AC heater controller 11 and the wall outlet. Electrical wire 16 (all groups) varies in diameter depending on the intended current it carries—an example of which (copper wire insulated with PTFE) is in Table A and is purchased as a commercial component.

Heater plate 17 is designed to support and evenly disburse heat from heater 4 (flexible heater with pressure sensitive adhesive on one side). Heater 4 should be made from a good thermally conductive material such as aluminum, which has been anodized (plated) to resist corrosion.

Intended Use for Alternative Embodiment

Treatment apparatus B creates a volume which contains and heats a solution around infected nail(s) to amplify the keratolytic properties of the solution to theoretically imbed the solution within the nail molecular structure, in addition to etching the nail from the top.

To use treatment apparatus B, infected nail(s) are inserted into enclosures shown in FIGS. 5-7. All fasteners are tightened, preferably creating a liquid tight seal, to force saturated sponge 5 against the infected nail(s). The procedure is preferably continued for a therapeutically effective time period, typically about 20 to 30 minutes daily. The appropriate nail infection agent is added to reservoir 1 which fills sponge 5 and the appropriate volumes formed inside the enclosures with the agent.

For portable operation, battery pack 13 and battery heater controller 12 are strapped to the appropriate limb using leg harness 14. Electrical connection 16B is made between battery pack 13 and battery heater controller 12. Electrical connection 16A is also made between battery heater controller 12 and heater 4. The appropriate temperature is selected by rotating the dial on the battery heater controller 12. To remove the invention, the battery heater controller 12 is turned off. Solution is removed from the volumes using aspiration or gravity. Fasteners are loosened and the nail(s) are removed.

For stationary operation, heater controller 11 is plugged into a standard wall outlet using electrical connection 16C. Electrical connection 16A is also made between heater controller 11 and heater 4. The appropriate temperature is selected by rotating the dial on the heater controller 11. To remove the invention, the heater controller 11 is turned off. The solution is removed from the volumes using aspiration or gravity. Fasteners are loosened and the nail(s) are removed.

Discussion of Typical Nail Infection Agents, Times and Temperatures

The terms tinea unguium and onychomycosis specifically refer to fungal infections of the toe nails. These infections, however, may be caused by different fungi such as: *Trichophyton rubrum* and *Trichophyton mentagrophytes*, which are the major two.

Most successful antifungal agents such as ciclopirox and Anacor AN2690 are broadband antifungal agents which means they are effective in treating a wide range of fungi responsible for onychomycosis.

However, even a broad band antifungal agent is ineffective in treating onychomycosis without contacting the fungus. To facilitate this contact, the antifungal agent (and a keratolytic agent such as salicylic acid) are dissolved in warm water (45 degrees C.).

The infected nails are submerged in the warm solution mixture for 20 to 30 minutes daily. Since human nails are made of keratin, and keratin absorbs water, the antifungal agent becomes embedded inside the nail, contacting the fungus.

Additional topical treatments (such as a topical antibiotic ointment over undecyclenic acid) are applied after the water has evaporated to further create a toxic environment for the fungi.

TABLE A

| ITEM NO | DESCRIPTION | QUANTITY | MFG/SUPPLIER | REF PART NO |
|---|---|---|---|---|
| 1 | Reservoir | 1 | mcmaster.com | 7510A656 |
| 2 | Diaper Enclosure | 1 | mcmaster.com | 58435T11 |
| 3 | Fluid Tubing | A/R | mcmaster.com | 50375K41 |
| 4 | Heater | 1 | mcmaster.com | 35765K126 |
| 5 | Sponge | 1 | mcmaster.com | 7271T32 |
| 6 | Toe Harness | 1 | custom | N/A |
| 7 | Enclosure | 1 | custom | N/A |
| 8 | Enclosure Cover | 1 | custom | N/A |
| 9 | Hex Nut | 4 | mcmaster.com | 90730A003 |
| 10 | Spring | 4 | mcmaster.com | 9657K81 |
| 11 | AC Heater Controller | 1 | mcmaster.com | 35655K89 |
| 12 | Battery Heater Controller | 1 | mcmaster.com/ custom | mod of 35655K89 |
| 13 | Battery Pack | 1 | sears.com | 911022000 |
| 14 | Leg Harness | 1 | mcmaster.com | 8062T211 |
| 15 | Threaded Rod | 4 | mcmaster.com | 93250A105 |
| 16 | Electrical Wire | A/R | mcmaster.com | 1749T23 |
| 17 | Heater Plate | 1 | custom | N/A |
| 18 | Heat Transfer Device | 1 | mcmaster.com | 7789A11 |
| 19 | Heater Cover | 1 | custom | N/A |
| 20 | Sponge Harness | 1 | custom | N/A |
| 21 | Sodium Polyacrylate Liner | 1 | mcmaster.com | 7271T32 |
| 22 | Opening | 1 | custom | N/A |

The above descriptions may have used terms such as above, below, top, bottom, over, under, et cetera. These terms are used to aid understanding of the invention are not used in a limiting sense.

While the present invention is disclosed by reference to the preferred embodiments and examples detailed above, it is to be understood that these examples are intended in an illustrative rather than in a limiting sense. It is contemplated that modifications and combinations will occur to those skilled in the art, which modifications and combinations will be within the spirit of the invention and the scope of the following claims.

Any and all patents, patent applications and printed publications referred to above are incorporated by reference.

What is claimed is:

1. Apparatus for treating an infected nail of a digit of a patient comprising:

an enclosure that functions to (i) house at least a distal end of at least one digit of a patient having an infected nail; and (ii) contain a nail infection agent-containing member or sponge member comprising a nail infection agent and positionable against the infected nail at the distal end of the digit housed within the enclosure;

a heater member maintained against and in a heat-transfer relationship with the nail infection agent; whereby the heated nail infection agent is adapted to be applied to and maintained against the infected nail by the nail infection agent-containing member for a therapeutically effective period of time; and, a pressure application component specifically designed to provide a localized pressure that forces (i) the heater member against the nail infection agent-containing member or sponge member and (ii) the nail infection agent-containing member or sponge member against the infected nail; wherein, the application of pressure facilitates maintaining the nail infection agent against the infected nail for the therapeutically effective period of time; wherein, the pressure application component adjustably attaches the nail infection agent-containing member or sponge member, and the heater member, within the enclosure to allow for an adjustment of the position of the members, wherein the adjustment is a movement of the members relative to a dorsal surface of the infected nail to provide the localized application of pressure on the infected nail;

whereby, the apparatus facilitates a trans-keratin drug delivery of the nail infection agent through the infected nail in a dark, warm, and moist environment that prevents the growth of fungi in the infected nail.

2. The apparatus according to claim 1 further comprising a supply of the nail infection agent operably coupled to the agent-containing member for supplying and re-supplying the agent-containing member with the nail infection agent during the treating of the infected nail.

3. The apparatus according to claim 1 wherein the nail infection agent comprises a flowable, aqueous nail infection agent that functions as a keratolytic agent.

4. The apparatus of claim 1, wherein:
the enclosure comprises a means for housing at least the distal end of the at least one digit of the patient having the infected nail;
the nail infection agent-containing member or sponge is configured to be placed in contact with the infected nail using means, within the housing means, for positioning the nail infection agent-containing member or sponge against the infected nail at the distal end of the digit housed within the enclosure; and
the heater member comprises means for heating the nail infection agent, whereby the heating means is maintained against and in a heat-transfer relationship with the nail infection agent;
whereby, the nail infection agent-containing member or sponge functions to maintain the heated nail infection agent against the infected nail for a therapeutically effective period of time; and,
whereby, the apparatus facilitates a trans-keratin drug delivery of the nail infection agent through the infected nail in a dark, warm, and moist environment that prevents the growth of fungi in the infected nail.

5. The apparatus according to claim 4 further comprising means for restraining the aqueous nail infection agent from coming into contact with the patient's skin.

6. The apparatus according to claim 4 further comprising means for supplying the nail infection agent-containing member with the nail infection agent while the distal end of the digit is housed within the enclosure.

7. The apparatus according to claim 4 further comprising means for restraining the aqueous nail infection agent from escaping from the enclosure.

8. A method for treating an infected nail of a digit of a patient comprising:
obtaining the apparatus of claim 1;
housing within the enclosure at least the distal end of at least the one digit of the patient having the infected nail;
contacting the infected nail with the nail infection agent by positioning the nail infection agent-containing member or sponge against the dorsal surface of the infected nail;
enhancing the penetration of the nail infection agent into the infected nail by maintaining the heater against and in a heat-transfer relationship with the nail infection agent thereby heating the nail infection agent; and
maintaining the heated nail infection agent against the infected nail for a therapeutically effective time period;
whereby, the method facilitates a trans-keratin drug delivery of the nail infection agent through the infected nail in a dark, warm, and moist environment that prevents the growth of fungi in the infected nail.

9. The method according to claim 8 further comprising restraining the nail infection agent from coming into contact with the patient's skin.

10. The method according to claim 8 further comprising supplying the agent-containing member with the nail infection agent while the digit is housed within the enclosure.

11. The method according to claim 8, wherein the contacting step is carried out by first applying a keratolytic agent to open the nail structure and then applying the nail infection agent to the dorsal surface of the infected nail.

12. A system for treating an infected nail, comprising:
a drug delivery mechanism comprising a nail infection agent and a heater for heating the nail infection agent, wherein the heater has a surface adapted for contacting, and conducting heat into, a nail infection agent-containing member or sponge that is positionable for direct contact with an infected nail of a digit of a subject; and,
an enclosure for housing and releasably attaching the drug delivery mechanism to the digit having the infected nail and maintaining the direct contact between the heating element and the nail infection agent-containing member or sponge member containing the nail infection agent, wherein the maintaining includes applying a localized pressure that forces (i) the heater member against the nail infection agent-containing member or sponge member and (ii) the nail infection agent-containing member or sponge member against the infected nail for a therapeutically effective period of time;
wherein the enclosure comprises a pressure application component, the pressure application component adjustably attaches the nail infection agent-containing member or sponge member, and the heater member, within the enclosure to allow for an adjustment of the position of the members, wherein the adjustment is a movement of the members relative to a dorsal surface of the infected nail to provide the localized application of pressure on the infected nail; and
wherein, the system facilitates a trans-keratin drug delivery of the nail infection agent through the infected nail in a dark, warm, and moist environment that prevents the growth of fungi in the infected nail.

13. The system of claim 12, wherein the heating element heats the nail infection agent to a temperature of about 45° C. at the dorsal surface of the nail.

14. The system of claim 12, wherein the nail infection agent comprises a keratolytic agent.

15. The system of claim 14, wherein the keratolytic agent comprises salicylic acid.

16. A method of treating an infected nail of a subject, wherein the method comprises:
obtaining the system of claim 12;
applying the nail infection agent to the dorsal surface of the infected nail using a nail-infection-agent-containing member or sponge for receiving and delivering the anti-infective agent to the infected nail;
releasably attaching the enclosure to the digit having the infected nail, wherein the releasably attaching includes contacting the nail-infection-agent-containing member or sponge with the dorsal surface of the infected nail; and,
applying heat to the nail infection agent by maintaining contact between the nail-infection-agent-containing member or sponge and the heating element for a therapeutically effective treatment time
wherein, the method facilitates a trans-keratin drug delivery of the nail infection agent through the infected nail in a dark, warm, and moist environment that prevents the growth of fungi in the infected nail.

17. The method of claim 16, wherein the heating element maintains a temperature of about 45° C. at the dorsal surface of the nail.

18. The method of claim 16, wherein the applying comprises treating the infected nail with a keratolytic agent.

19. An apparatus for treating a digit having an infected nail, wherein the apparatus comprises an enclosure and a heated drug delivery mechanism having a nail-infection-agent-containing member or sponge, a heating element, and a pressure application component; wherein,
the nail-infection-agent-containing member or sponge member, and the heating member, are adjustably attached to the pressure application component, wherein the pressure application component comprises a toe harness for supporting the plantar surface of the digit having the infected nail and an agent harness in a position opposing the toe harness, wherein the agent harness functions to hold the nail-infection-agent-containing member or sponge member;

a movement of the agent harness relative to the toe harness functions to apply a pressure to the dorsal surface of the infected nail, contact the dorsal surface of the infected nail with the infection-agent-containing member or sponge member, and releasably attach the digit having the infected nail to the apparatus for a therapeutically effective period of time; wherein, the pressure application component is specifically designed to provide a localized pressure that (i) forces the heating member against the nail infection agent-containing member or sponge member to created the heated drug delivery mechanism, and (ii) forces the heated drug delivery mechanism against the infected nail to maintain the nail infection agent against the infected nail for the therapeutically effective period of time; and, the enclosure (i) contains the heated drug delivery mechanism and (ii) facilitates a trans-keratin drug delivery of the nail infection agent through the infected nail in a dark, warm, and moist environment that prevents the growth of fungi in the infected nail.

* * * * *